United States Patent [19]

Reimels

[11] Patent Number: 4,548,207
[45] Date of Patent: Oct. 22, 1985

[54] DISPOSABLE COAGULATOR

[75] Inventor: Harry G. Reimels, Braintree, Mass.

[73] Assignee: Mentor O & O, Inc., Hingham, Mass.

[21] Appl. No.: 442,261

[22] Filed: Nov. 17, 1982

[51] Int. Cl.$^4$ ............................................. A61B 17/39
[52] U.S. Cl. ............................ 128/303.17; 128/303.18;
206/363; 219/234
[58] Field of Search .................... 128/303.13, 303.14,
128/303.17, 303.18, 303.19, 784, 642; 219/227,
229, 233, 234; 206/363

[56] References Cited

U.S. PATENT DOCUMENTS

| | | | |
|---|---|---|---|
| 1,983,669 | 12/1934 | Kimble | 128/303.17 |
| 3,682,162 | 8/1972 | Colyer | 138/303.18 X |
| 3,801,766 | 4/1974 | Morrison, Jr. | 219/234 X |
| 3,825,004 | 7/1974 | Durden | 128/303.17 X |
| 4,014,343 | 3/1977 | Esty | 128/303.14 |
| 4,043,342 | 8/1977 | Morrison, Jr. | 128/303.14 |
| 4,112,950 | 9/1978 | Pike | 128/303.14 |
| 4,248,231 | 2/1981 | Herzog et al. | 128/303.17 X |
| 4,476,862 | 10/1984 | Pao | 128/303.17 |
| 4,483,338 | 11/1984 | Bloom et al. | 128/303.18 |

FOREIGN PATENT DOCUMENTS 132880 11/1932 Fed. Rep. of
Germany ..................... 128/303.18

Primary Examiner—Lee S. Cohen
Attorney, Agent, or Firm—Morse, Altman & Dacey

[57] ABSTRACT

A disposable coagulator for the bipolar coagulation of blood vessels and/or tissue is disclosed. The disposable coagulator comprises a light-weight, electrically insulating housing, a coaxial probe defining an inner and outer electrode and having a beveled end and secured within the housing, and a pair of insulated leads coupling the probe to a source of variable rf power. The surface area of the inner electrode at the beveled end is substantially the same as the surface area of the outer electrode. Preferably, the housing is injection formed of a suitable plastic material in two parts designed to snap-fit to one another so as firmly to hold the probe within the housing, once assembled.

4 Claims, 7 Drawing Figures

DISPOSABLE COAGULATOR

BACKGROUND OF THE INVENTION

1. Field of the Invention

The present invention relates generally to coagulators and, more particularly, to a disposable coagulator for the bipolar coagulation of blood vessels and/or tissue.

2. The Prior Art

Coagulators as herein referred to are electro-surgical instruments designed for the coagulation of blood vessels and/or tissue. For the most part, such coagulators are of the wet field type, i.e., there is no requirement to clear bood and/or other fluid from the operating field before using the coagulator; in fact wet field type coagulators work better in a wet field.

Initially, such wet field coagulators were of the mono-polar kind. In a mono-polar coagulator, the current flows from the instrument randomly through the body to a ground plate placed on the patient distant from the operative site. This can, on occasion, produce a ground plate burn. Additionally, the mono-polar coagulator can be responsible for cross-cardiac difficulties.

To overcome these difficulties, bipolar coagulators have been developed. Bipolar coagulators essentially are forceps employing a two-point coagulation technique with two forceps blades insulated from one another. The coagulating current passes from one forceps tip to the other, so only the vessel and/or tissue held between the tips is coagulated. This pinpoint coagulation results in less surrounding tissue being damaged, and the need for a ground plate is eliminated. Bipolar coagulation has been found particularly advantageous in ophthalmic surgery, ear-nose-throat (ENT) surgery, plastic surgery, neurosurgery, orthopaedic surgery, cardiovasuclar surgery and thoracic surgery, where in each instance precise hemostasis is critical. See S. D. McPherson, Jr., M.D. "Bipolar Coagulation in Ophthalmic Operations," *Am. J. of Ophthalmology*, 73:5, 1972; K. Reed, M. D. and C. J. Snider, M.D. "Bipolar Forceps for Electrocautery in Tonsillectromy," *Transactions*, Vol. 78, July-Aug., 1974, No. 4; S. Charles, M.D., J. White, C. Dennison and D. Eichenbaum, M. D. "Bimanual, Bipolar Intraocular Diathermy," *Am. J. of Ophthalmology*, 81:1, 1976; and M. A. Kass, M.D., S. D. Hersh, M.D. and D. M. Albert, M.D. "Experimental Iridectomy with Bipolar Microcautery," *Am. J. of Ophalmology*, 81:4, 1976.

Bipolar coagulation, as heretofore practiced, does have its share of drawbacks, however. For one, it is dependent on the user's skill, dexterity and absence of fatigue in manually positioning, with just the correct force and separation, the two forceps blades about the vessel or tissue to be coagulated and for holding it there during the time period that the coagulating current is passed therebetween. In addition to effecting and maintaining exacting control of the area to be coagulated, which is no easy task in view of the smallness of such an area, usually measured in millimeters or fractions thereof, the user has to repeat the coagulation process several times, perhaps many times until all areas in the operative site have been coagulated. The user, at best, can only approximate the sameness in the force and separation of the two forceps blades as he goes on coagulating one affected area after another. Yet, the distances separating the tips of the forceps have a direct bearing on the power requirements for the instrument. For, with a wider separation between the tips of the forceps, more power will be required to effect a good coagulation than with a narrower separation.

While power settings of the coagulator can be changed in between coagulations, the power settings cannot be changed during the time period that the coagulation current is passed between the forceps tips. Further, for the user to keep changing the power settings even in between coagulations is, at best, an unwelcome distraction from the task at hand. For the most part, surgeons like to stick with the power settings they set for most, if not all, the coagulation they do at a given operative site. Consequently, since there is bound to be variations, however slight, between successive coagulation spacings separating the forceps tips, the resultant tissue coagulation will vary in terms of unwanted tissue damage to the surrounding tissue. Thus, the lesion produced from one coagulation to the next will be different.

Furthermore, tissue to metal adhesion at the tips of the forceps is at times a problem, stemming in part from the difficulty in smoothly polishing the forceps tips, particularly if they have a hard carbide surface. Also, when pressing a vessel or tissue together, the surgeon may unwittingly short out the coagulating current between the tips by in fact forcing portions of the conducting forceps blades into contact with each other. Still further, the coagulator forceps are expensive to make and must be sterilized after each operative use.

SUMMARY OF THE INVENTION

It is a principal object of the present invention to overcome the above disadvantages by providing a coagulator of improved construction for the bipolar coagulation of blood vessels and/or tissue.

More specifically, it is an object of the present invention to provide a coagulator for the bipolar coagulation of blood vessels and/or tissue, which coagulator is disposable and comprises a housing formed of an insulating material, a coaxial probe defining and inner and an outer electrode and provided with a beveled end, the probe with its beveled end extending from the housing at one end thereof, a pair of contact pins also secured in the housing but extending therefrom at its other end, and a pair of wires connecting the inner and outer electrodes of the probe to the contact pins. A pair of insulated flexible leads couple the respective electrodes of the probe to a source of variable radio frequency (rf) power. Preferably, the housing is light-weight and is injection formed of a suitable plastic material in two parts designed to snap-fit to each other. For best results, the exposed surface area of the inner electrode at the beveled end is substantially the same as the exposed surface area of the outer electrode. Preferably, the disposable coagulator is contained, once sterilized, in a wrapper. Preferably, the beveled end of the probe is smoothly polished and is beveled at an angle between about 30° to about 60°. Preferably, the coaxial probe is formed of a corrosion resistant metal alloy, such as stainless steel. The disposable coagulator is characterized by having a uniform gap between its inner and outer electrodes and by being light-weight and inexpensive to manufacture.

Other objects of the present invention will in part be obvious and will in part appear hereinafter.

The invention accordingly comprises the disposable coagulator of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENT

Figure 7:
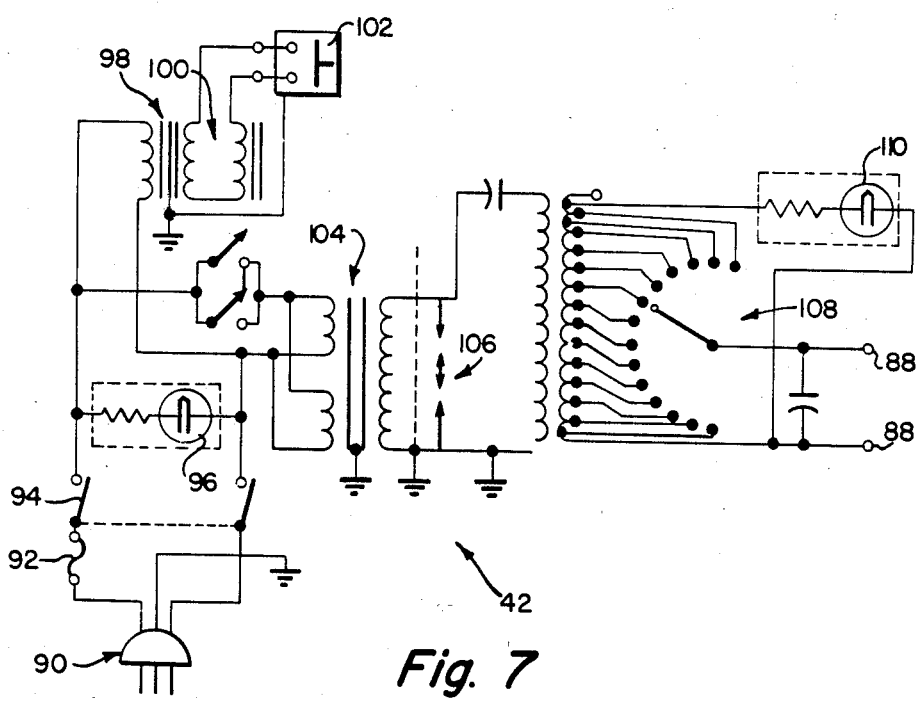
FIG. 7 is a schematic diagram of a preferred source of variable rf power for the disposable coagulator of FIG. 1.

Generally, the illustrated embodiment of a disposable coagulator 10 for the bipolar coagulation of blood vessels and/or tissue comprises a housing 12 formed, along its axial length 14, of two parts, a bottom part 16 and a top part 18, a coaxial probe 20 defining an inner electrode 22 and an outer electrode 24 and having a beveled end 26 and secured within the housing 12, a pair of contact pins 28, 30 also secured within the housing 12, and a pair of wires 32, 34 connecting the respective electrodes 22 and 24 of the probe 20 to the pair of contact pins 28 and 30. A flexible cable 36, containing a pair of insulated leads 38 and 40, couples the respective electrodes 22 and 24 of the probe, via the contact pins 28 and 30, to a source 42 of variable rf power, shown in FIG. 7. Preferably, the disposable coagulator 10 is contained, for storage and/or shipment, in sterilized condition and ready for use, in a suitable transparent plastic wrapper 44. Other containers also can be used.

The housing 12 preferably is injection formed of a suitable plastic material that is hard yet flexible, is chemically almost totally inert, and is non-wettable by any liquid found at an operative site, such as blood and other body fluids and electrolytes such as saline, or any combination thereof. One preferred plastic material exhibiting these desired characteristics is Teflon (polyperfluoroethylene). Other preferred plastic materials include polyvinyl chloride, polyethylene and urea-formaldehyde.

Figure 5:
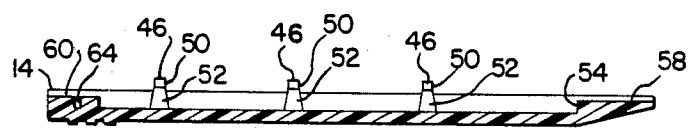
FIG. 5 is a section along the line 5—5 and in the direction of the arrows of FIG. 2.
Figure 6:
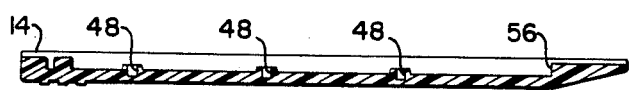
FIG. 6 is a view similar to FIG. 5 but showing a complementary part of the disposable coagulator of FIG. 1.

The housing 12 furthermore is formed so that the bottom and top parts 16 and 18 snap-fit to one another. To this end, these parts 16 and 18 respectively are provided with complementary mating members designed to engage each other, as may be best observed in FIGS. 5 and 6. These complementary mating members comprise a number of protrusions 46 formed in the bottom part 16 and a corresponding number of depressions 48 formed in the top part 18. Each of these protrusions 46 is formed with a depression-engaging cylindrical end portion 50 and a tapered stem 52, tapered for extra strength and stability. It is the cylindrical end portions 50 which enter into and frictionally engage the walls of the cylindrical depressions 48 whose internal diameters are somewhat greater than that of the end portions 50.

Each part 16 and 18 of the housing 12 also is formed with a hollow interior 54 and 56, respectively, and with a complementary central groove 58 at the front and a pair of complementary off-center grooves 60 and 62 at the rear, each communicating with the hollow interiors 54 and 56. Each off-center groove 60 and 62 furthermore is formed with a transverse slot 64 and 66, respectively. These slots 64 and 66 are intended to accept projections 29 and 31 formed on pins 28 and 30 so as to locate the pins axially.

Figure 3:
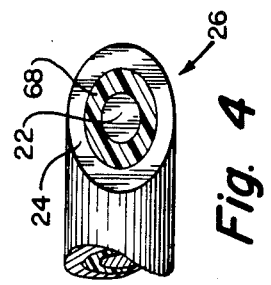
FIG. 3 is a plan view of other parts of the disposable coagulator of FIG. 1.
Figure 4:
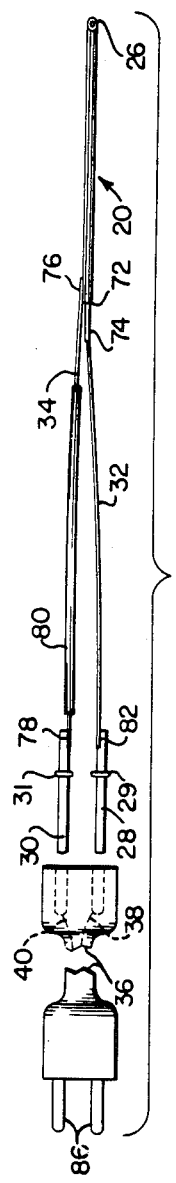
FIG. 4 is a view, on an enlarged scale, of a portion of one part shown in FIG. 3.

The electrical parts of the disposable coagulator 10 are best disclosed in FIGS. 3 and 4. They include the coaxial probe 20 defining the inner electrode 22 and the outer electrode 24, the pair of contact pins 28 and 30 and the pair of wires 32 and 34 respectively connecting the electrodes 22 and 24 with the pins 28 and 30.

The coaxial probe 20 preferably is formed with the inner electrode 22 and the wire 32 constituting an integral unit. This is followed by surrounding the front portion of the integral unit with a plastic shrink tube 68, preferably made from Teflon, which is subjected to a shrink treatment so as snugly to envelope the inner electrode 22. Then a tube forming the outer electrode 24 is slipped over the now combined inner electrode 22 and surrounding plastic shrink tube 68 and made snugly to envelope the latter. This can be accomplished in various ways. One preferred way of accomplishing it is by applying a penetrating cyanoacrylate adhesive so that capillary action draws it into contact between the shrink tube 68 and the outer electrode 24, thereby securing the assembly.

Thereafter, the end is beveled, as at 26, by grinding it down to the desired angle 70 ($\alpha$), which can be anywhere from about 30° to about 60°. This angle 70 at the beveled end 26 is for the convenience of the surgeon who, for the most part, is working with the aid of a microscope. The presence of the microscope in turn requires that he holds and manipulates all instruments, including the disposable coagulator 10 of the invention, at an angle with respect to the operative site.

At the other end of the coaxial probe 20, the wire 32 is bent, as at 72, and provided with a plastic sleeve 74 to serve as an insulator. The end of the outer electrode 24, on the other hand, is slit a short distance and then bent away from the wire 32. One end of the other wire 34 is spotwelded, as at 76, to the end of the electrode 24. The other end of the wire 34 is spotwelded, as at 78, to the contact pin 30. To prevent accidental shorting, either or both wires 32 and 34 preferably are enclosed substantially along their axial lengths by a plastic sleeve 80. The free end of the wire 32 also is spotwelded, as at 82, to the other contact pin 28.

Figure 2:
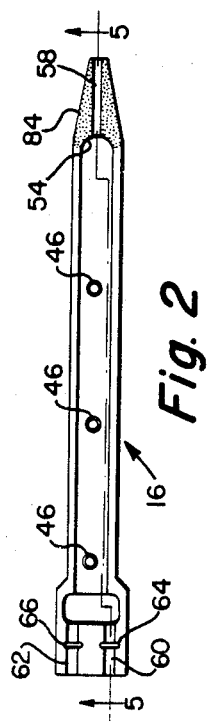
FIG. 2 is a plan view of a part of the disposable coagulator of FIG. 1.

The above-described electrical parts of the disposable coagulator 10, once assembled, are placed, as a unit, into the hollow interior 54 of the bottom part 16 of the housing 12. Preferably, the front ends of both parts 16 and 18 have been pre-coated with a suitable adhesive layer 84, observe FIG. 2. The coaxial probe 20 will fit snugly into the central groove 58, while the contact pins 28 and 30 will fit snugly into the off-center grooves 60, and 62, respectively, at the other end of the bottom part 16. Care should be taken that the protrusions 46 protrude in between the two wires 32 and 34.

Figure 1:
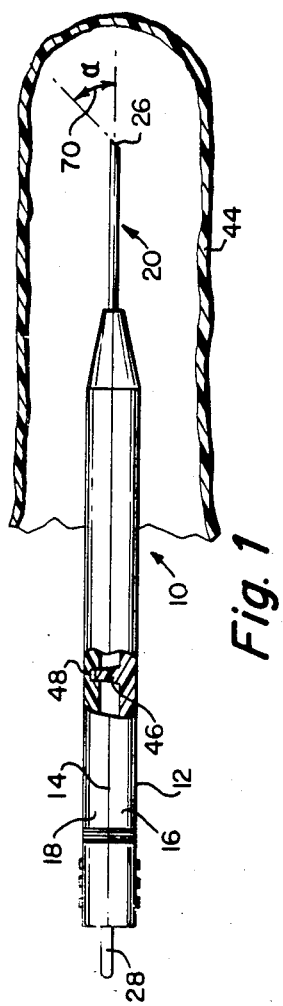
FIG. 1 is a side elevation, with a part in section, of a disposable coagulator constructed in accordance with the present invention.

With the electrical parts in place in the bottom part 16 of the housing 12, the disposable coagulator 10 is assembled by snap-fitting the top part of the housing 12 to the bottom part 16 thereof. With the two parts 16 and 18 properly assembled along their axial lengths 14, the thereby completed housing 12, with the aid of the adhesive layer 84, will firmly hold the coaxial probe 20 in place and projecting therefrom, as may be best observed in FIG. 1. Following assembly, the disposable coagulator 10 is sterilized, as for example by autoclaving, prior to being enclosed in its plastic wrapper 44.

In use, after the disposable coagulator 10 is removed from its wrapper 44, it is coupled, via the flexible cable 36, to the source 42 of variable rf power. This coupling is effected by inserting the plugs 86 of the cable 36 into the power output jacks 88 of the source 42, observe FIG. 7.

The illustrated preferred source 42 of variable rf power has been specifically designed for bipolar coagulation. The source 42 basically is a damped wave spark unit that provides a completely isolated output so that, with the source 42 properly grounded, there is low ground leakage from either electrode connection. The output wave-form is shaped by matching transformer impedance to the values of the rest of the circuitry, resulting in an output wave-form that causes minimal muscle stimulation for the amount of coagulation achieved. The source 42 comprises a grounded power cord 90, featuring a fuse 92, a power switch 94, a power pilot light 96, a relay transformer 98, a relay RBM 100 operable by a foot switch 102, a power transformer 104 having a spark gap assembly 106 connected across its secondary, and a variable output switch and coil assembly 108, featuring a generator light 110. The source 42 can be used with either a 110 VAC 60 Hz power or a 220 VAC 50 Hz power.

In use, after the disposable coagulator 10 has been coupled to the source 42 as above described, the source 42 is activated by turning the power switch 94 on. That the source 42 is on is ascertainable by observing that the power pilot light 96 is lit. Next, the surgeon selects the desired rf power setting by rotating the output switch 108. It is advisable to begin with a lower setting and then adjusting upward as may be required. Care should be taken not to use power settings which are in excess of that needed to coagulate.

The surgeon activates the disposable coagulator 10 by depressing the fott switch 102. He can observe that rf power is being delivered to the disposable coagulator 10 by noting that the generator light 110 is lit. As long as the surgeon keeps depressing the foot switch 102, rf power continues to be delivered to the disposable coagulator 10 and the generator light 110 will remain lit. If he wishes to adjust the power setting, whether up or down, the surgeon must first release the foot switch 102, thus interrupting the delivery of rf power to the coagulator 10.

The disposable coagulator 10 of the invention also is light-weight, of small dimension and, more importantly, is very convenient to use. For one, the surgeon is no longer handling a two blade, flexing instrument, such as most coagulator forceps heretofore used. For another, the surgeon no longer needs to control the distance separating the tips of the forceps and to hold that distance with the same force, during each and every succeeding coagulation. The surgeon now works with a uniform gap between the inner electrode 22 and the outer electrode 24—he can thus readily observe what he is doing. In view of this uniform gap between the electrodes 22 and 24, the surgeon can more readily determine the required rf power setting, which, once determined, remains the same. Following completion of the operation, the disposable coagulator 10 is discarded, for it is less costly to use a new one the next time than cleaning, re-sterilizing and repackaging the old.

Thus it has been shown and described a disposable coagulator 10 designed for the bipolar coagulation of blood vessels and/or tissue, which coagulator 10 satisfies the objects and advantages set forth above.

Since certain changes may be made in the present disclosure without departing from the scope of the present invention, it is intended that all matter described in the foregoing specification or shown in accompanying drawings, be interpreted in an illustrative and not in a limiting sense.

What is claimed is:

1. A disposable coagulator comprising:
   (a) a housing formed of an insulating material;
   (b) a coaxial probe defining an inner electrode and an outer electrode and having a beveled end and secured within said housing, with said beveled end extending therefrom at one end of said housing;
   (c) a pair of contact pins also secured within said housing but extending therefrom at its other end;
   (d) a pair of wires connecting said inner and outer electrodes of said coaxial probe to said pair of contact pins;
   (e) a wrapper containing said housing, said coaxial probe, said pair of contact pins, and said pair of wires in sterilized condition;
   (f) said housing being formed, along its axial length, of two parts snap-fit to one another so as firmly to hold said coaxial probe therebetween, said two parts being injection formed of a plastic material and provided with complementary mating members snap-fit to each other so as to secure said two parts of said housing to one another along its said axial length; and
   (g) an adhesive layer applied to at least one of said parts in the vicinity surrounding said coaxial probe, said adhesive layer cooperating with said two parts to firmly hold said coaxial probe in place.

2. The disposable coagulator of claim 1 wherein said two parts are formed with complementary central grooves and a pair of off-center cavities at their respective ends so as to embed respectively therein said coaxial probe at one end and said pair of contact pins at the other end when said two parts are snap-fit to one another, said complementary mating members comprising at least two protrusions on one of said two parts and at least two depressions on the other of said two parts, with said protrusions extending from said one of said two parts along a median line thereof and in a direction normal thereto.

3. The disposable coagulator of claim 1 wherein said beveled end of said coaxial probe is smoothly polished and beveled at an angle between about 30° to about 60°, said coaxial probe being formed with a plastic shrink tube electrically insulating said inner electrode from said outer electrode along its axial length, with one of said pair of wires being contiguous with and formed integral of said inner electrode and being spotwelded to one of said contact pins and the other of said pair of wires being spotwelded to said outer electrode at one end to the other of said contact pins at its other end.

4. The disposable coagulator of claim 1 wherein said inner and outer electrodes of said coaxial probe are formed of stainless steel and present a substantially equal surface area at said beveled end, said disposable coagulator being characterized by having a uniform gap between its said inner and outer electrodes and by being light-weight and inexpensive.

* * * * *